United States Patent [19]
Brunk et al.

[11] Patent Number: 5,433,837
[45] Date of Patent: Jul. 18, 1995

[54] GEL CASSETTE FOR ENHANCED ELECTROPHORETIC SEPARATION AND PROCESSES FOR THE PREPARATION THEREOF

[75] Inventors: Donald H. Brunk; Charles F. Collier, both of Wilmington; Charles W. Robertson, Rockland, all of Del.

[73] Assignee: E. I. Du Pont de Nemours and Company, Wilmington, Del.

[21] Appl. No.: 113,480

[22] Filed: Aug. 27, 1993

[51] Int. Cl.6 .................. G01N 27/26; G01N 27/447
[52] U.S. Cl. ............................ 204/299 R; 204/182.8
[58] Field of Search .............. 204/299 R, 182.8, 180.1

[56] References Cited

U.S. PATENT DOCUMENTS

| | | | |
|---|---|---|---|
| 3,129,158 | 4/1964 | Raymond et al. | 204/299 R |
| 4,576,693 | 3/1986 | Kreisher et al. | 204/180.1 |
| 4,631,120 | 12/1986 | Pohl | 204/182.8 |
| 4,631,122 | 12/1986 | Pohl | 204/299 R |
| 4,717,653 | 1/1988 | Webster, Jr. | 435/5 |
| 4,729,823 | 3/1988 | Guevara, Jr. | 204/299 R |
| 4,885,697 | 12/1989 | Hubner | 364/497 |
| 5,087,558 | 2/1992 | Webster, Jr. | 435/5 |
| 5,234,559 | 8/1993 | Collier et al. | 204/182.8 |

OTHER PUBLICATIONS

Anders Olsson et al. "Uniformly spaced banding pattern in DNA sequencing gels by use of field-strength gradient" Journal of Biochemical and Biophysical Methods 10 (1984) 83-90.

*Primary Examiner*—John Niebling
*Assistant Examiner*—John S. Starsiak, Jr.

[57] ABSTRACT

A gel cassette useful in electrophoretic separation of molecular fragments is disclosed, in which a gelatinous substrate is uniquely configured to concentrate similar separated fragments. Containment means is also disclosed which provides for the desired configuration of the substrate. The containment means further includes a cover design which locks into an open position to eliminate cross contamination. In addition, processes for the preparation of such cassettes and for use of the cassettes in separation and transfer apparatus are disclosed.

8 Claims, 4 Drawing Sheets

FIG. 4
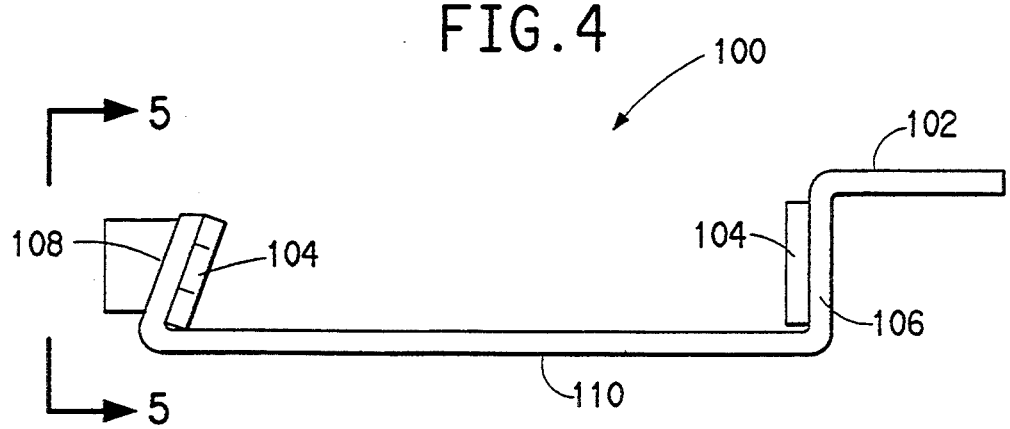
FIG. 5
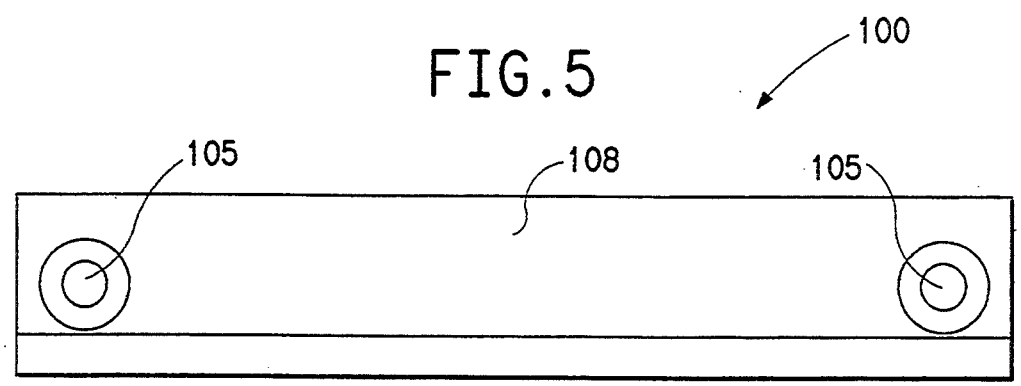
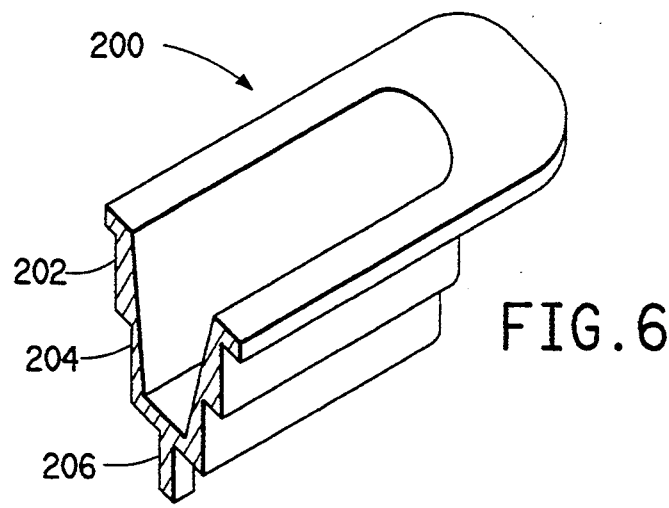
FIG. 6

5,433,837

GEL CASSETTE FOR ENHANCED ELECTROPHORETIC SEPARATION AND PROCESSES FOR THE PREPARATION THEREOF

FIELD OF THE INVENTION

This invention relates to the field of gel electrophoresis. More particularly, this invention relates to apparatus for separating molecular fragments across a gelatinous medium, and processes for the preparation thereof.

BACKGROUND OF THE INVENTION

Gel electrophoresis is a standard tool in molecular biology to separate molecular components, such as DNA, RNA or protein, either for subsequent identification or in a preparative procedure. In gel electrophoresis, the different mobility of ions under the influence of an electric field (a function of electrical charge and/or density) serves to separate molecular fragments as they traverse the porous medium. It is common to then transfer the separated fragments to a membrane that binds the fragments permitting further processing directed toward making an image ("blot") visible so that identification can be accomplished.

Ordinarily this transfer is done with the fragments of DNA or the like separated into bands distributed along the body of the gel. The driving force is removed when adequate separation has occurred. A membrane, usually a nylon, is placed on top of the gel so that the bands transfer laterally to the membrane. This is known as a Southern Blot and many variations are available.

An alternate procedure, direct blot, is described by Pohl in U.S. Pat. Nos. 4,631,120 and 4,631,122. There the DNA fragments are run to the end of the gel and transferred to a moving belt that is in contact with the end of the gel. Pohl teaches concentration by angled contact and programmed velocity. Pohl does not teach the use of a prepackaged and disposable gel cassette in conjunction with direct blot.

In U.S. Pat. No. 5,234,559 incorporated by reference herein, there is disclosed an improved direct blot process and apparatus in which the separated fragments are transferred from the end of the gel to a moving membrane that is held on a frame. The framed membrane is then subjected to the further manual or automatic processing steps required to make an image visible for identification such as the steps described in U.S. Pat. Nos. 4,717,653 and 5,087,558 by Webster, Jr. which can be followed by analysis such as that described by Hubner in U.S. Pat. No. 4,885,697.

For convenience of handling and to insure accurate alignment in use, the gel in the apparatus of that application is held in a cassette which is cleaned after each use and reused. It is one object of the instant invention to avoid cleaning and reuse by providing a prepackaged and disposable gel cassette. Prepackaged gels per se are known, but none are in a cassette for direct blot.

It is an object of the instant invention to provide a disposable gel cassette for direct blot procedures. It is a further object to provide such a cassette in a system in which the images obtained have bands which are well separated and with enhanced concentration. To that end the cassette of the instant invention provides an internal angle near the contact to reduce the gel thickness and concentrate the fragments. The apparatus of U.S. Pat. No. 5,234,559 in which the instant gel cassette is useful provides programmed velocity. Still further objects of the invention are to provide a gel cassette which is conveniently filled in the gel casting process, easily packaged for safe shipping, low cost, and convenient to insert into and remove from the apparatus in the field.

SUMMARY OF THE INVENTION

There is disclosed herein a gel cassette in which molecular fragments in a solution are separated electrophoretically therein, comprising:

(a) a gelatinous substrate containing the molecular fragments for separation at a first end thereof and configured sufficient to concentrate similar separated molecular fragments at a second end thereof; and (b) containment means which supports the gelatinous substrate.

The gelatinous substrate (a) further comprises a top surface to which the molecular fragments are added and a bottom surface which contacts the containment means. The top and bottom surfaces are essentially parallel to one another in the region of the first end and the top and bottom surfaces are essentially nonparallel (and preferably, tapered) to one another in the region of the second end so that the gelatinous substrate is narrower in cross section between the top and bottom surfaces at the second end than at the first end.

The containment means (b) further comprises a base portion supporting the substrate (a) along its bottom surface; a plurality of walls positioned essentially perpendicularly to the bottom surface to support peripheral portions of the substrate (a); a top portion bearing upon the top surface of the substrate; and a well portion positioned relative to the top surface suitable for casting integral wells within the substrate (a). These wells are adapted to contain the solution including molecular fragments for electrophoresis.

There is also disclosed herein a process for the preparation of a gel cassette for the electrophoretic separation of molecular fragments therein.

BRIEF DESCRIPTION OF THE DRAWINGS

FIG. 4 is a side elevational view of a holding fixture used for casting electrophoretic gel in the cassette of the invention and for the shipment thereof.

FIG. 5 is an end elevational view of the fixture of FIG. 4 on the line 5—5 of FIG. 4.

FIG. 6 is a perspective view, with an end elevational cross section, of a comb used with the cassette of the invention.

DETAILED DESCRIPTION OF THE INVENTION

Figure 1:
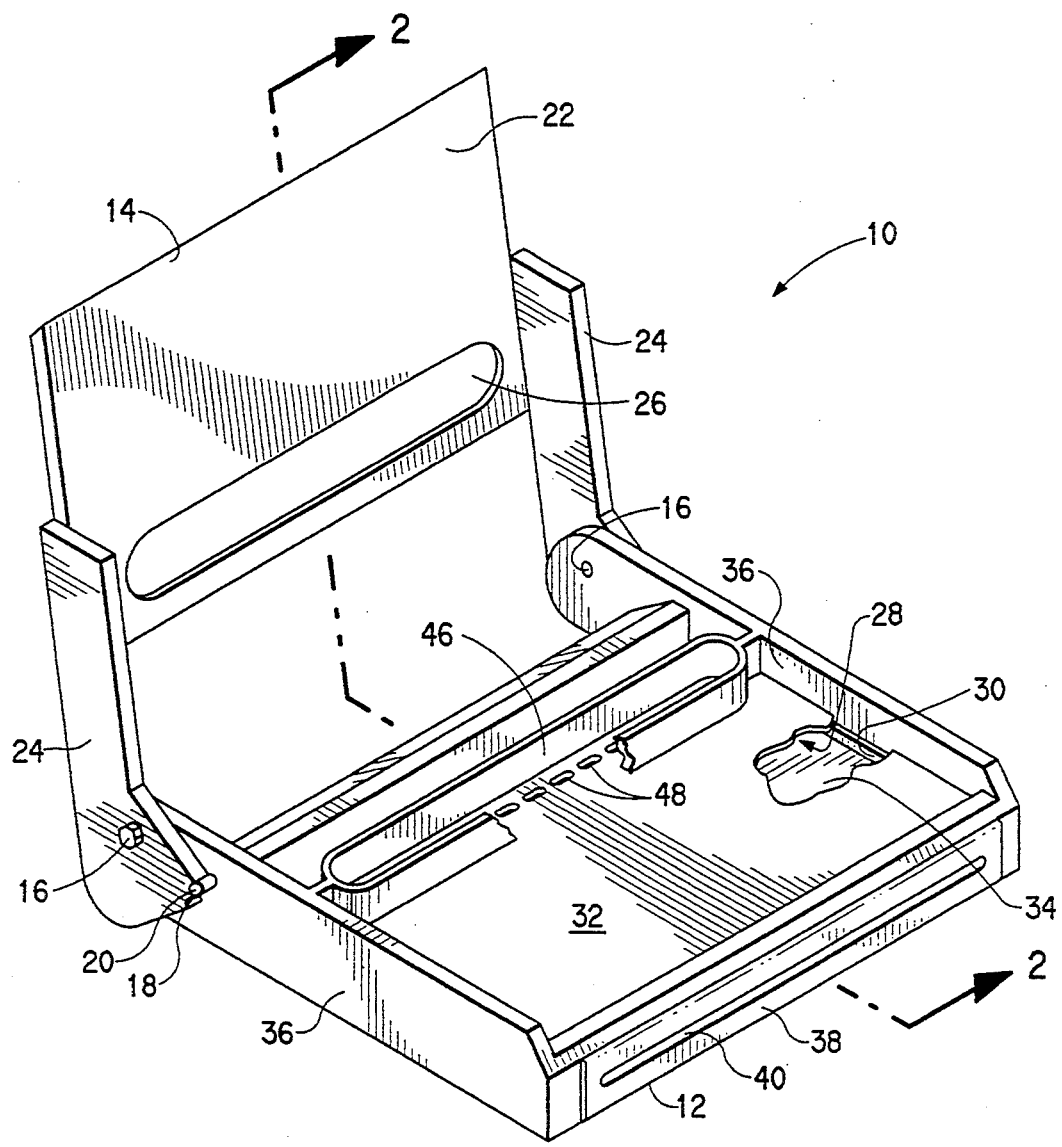
FIG. 1 is a perspective view, partly in cross-section, of a gel cassette according to the invention.

The gel cassette 10 of the invention is best seen in FIG. 1. It comprises a base 12, and a cover portion (lid 14) attached to base 12 by two hinge pivots 16. Lid 14 also acts as a handle to facilitate insertion of cassette 10 into processing apparatus. When lid 14 is in the open position a locking means, such as a notch 18 on lid 14 mating with a pin 20 on base 12, holds the two members in the open position. We prefer to use two such notch 18 and pin 20 arrangements, one on either side. We also contour the end of hinge pivots 16 so that they act as a bosses to bias the cassette into the proper position in the apparatus in which it is used.

The lid 14 comprises a flat top 22 and two lid side plates 24 which are contoured to receive hinge pivots 16 with holes 17 (not shown). A slot 26 forms an aperture in flat top 22 for a purpose to be explained. Reinforcing ribs 25 and 27 (not shown) stiffen lid 14.

Figure 2:
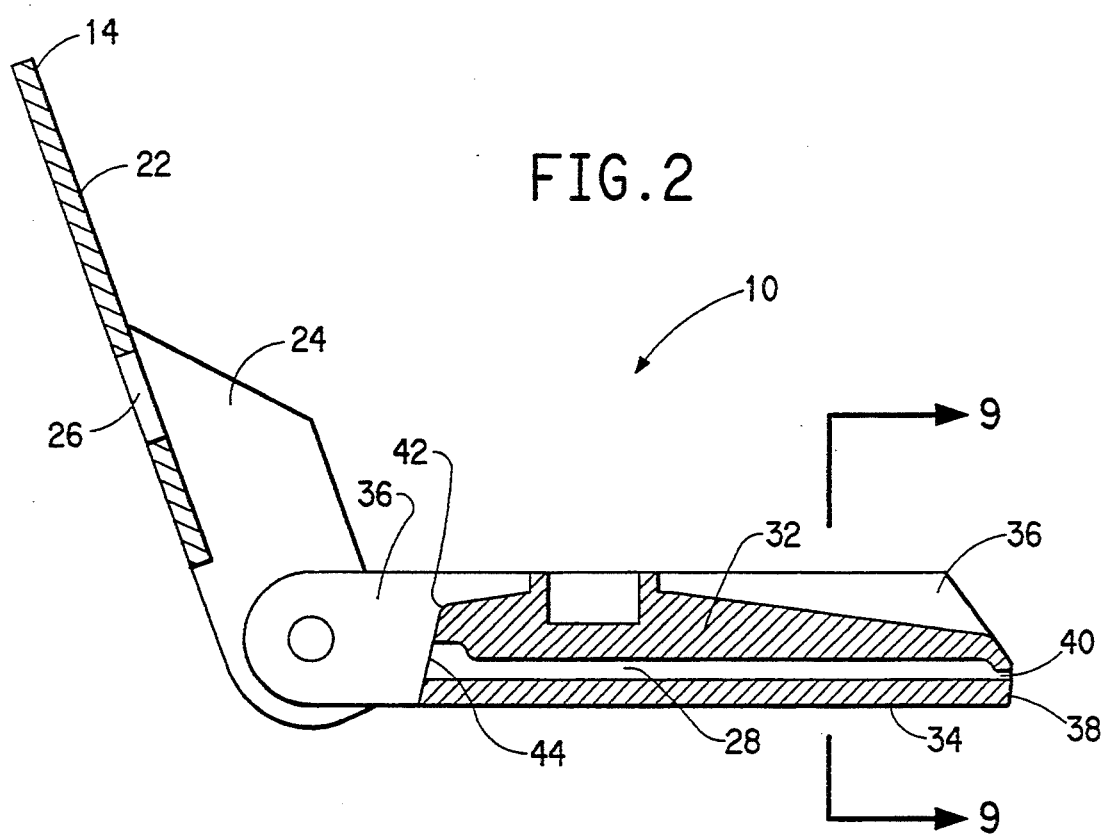
FIG. 2 is a cross-sectional view on the line 2—2 of FIG. 1.

Base 12 contains gel cavity 28 which is formed between a plurality of side walls 30 (only one of which is seen in FIG. 1), top wall 32, and bottom wall 34. Side walls 30 are spaced inwardly from side plates 36 which define the outer structure of base 12 and mount the hinges 16. The front of cavity 28 is closed by front wall 38 which is pierced by gel slot 40. The rear of gel cavity 28 is closed by rear wall 42 which is pierced by expanded gel entry port 44 (as seen in FIG. 2). The gel slot 40 and entry port 44 function to discharge electrophoretically separated components and to introduce gel to gel cavity 28, respectively. Atop top wall 32 there is located comb well 46, and top wall 32 within the confines of comb well 46 is apertured by well guides 48 for entry of the comb teeth 206 of the well-forming comb as will be seen. We use thirteen well guides 48 to create in the formed gel slab the desired number of lanes for electrophoresis. It should be noted that cavity 28 is tapered down to slot 40 by taper 41 which serves to concentrate the separated bands as electrophoresis is carried out from the wells formed by the comb which is held in place by the comb well 46 and the well guides 48 toward the slot 40 where it is transferred to a membrane moving in contact with front wall 38 upwardly (in use the cassette is held substantially horizontal with the cassette 10 oriented as shown in the figures).

Figure 7:
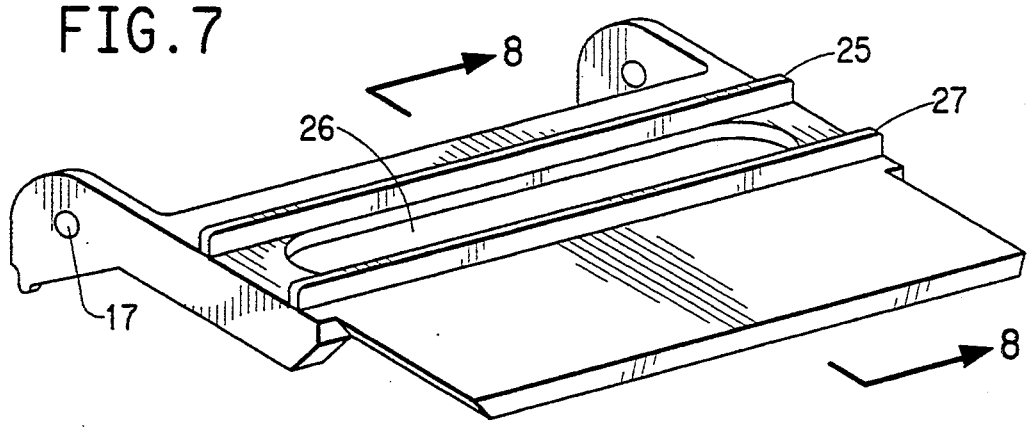
FIG. 7 is a perspective view of a preferred embodiment of the lid of FIG. 1.

Refer to FIG. 7. This embodiment is characterized by adding comb support ribs 29 and 31 on the side opposite reinforcing ribs 25 and 27. These serve to support comb 200 along the sides 202. See FIG. 6.

Figure 8:
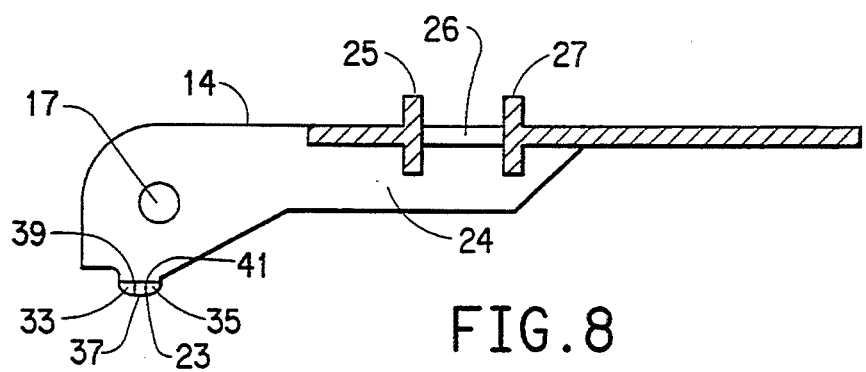
FIG. 8 is a cross-sectional view of the lid of FIG. 7 taken on the line 8—8 and showing details of a locking means.

Lid 14 preferably is configured so that when it is in the open position, which is the operating position, (see FIGS. 1 and 2) it is locked in place by pin 20 on base 12 being in notch 18. This is effected by having a locking angle in the relationship between the two coacting parts. To get the parts into this position requires that there be some means to cam the structure of lid side plate 24 past pin 20 as lid 14 is opened. The way we do this is shown in FIG. 8. Formed on the extreme tip 23 of plate 24 are two quarter cones 33, 35 separated by a flat 37. The apices of these cone structures are on flat 37 at points 39, 41. In operation, as lid 14 rotates about hinge pivot 16 in hole 17, the beveled end of pin 20 contacts quarter cone 35 and slides on its surface camming the extreme tip 23 of lid side plate 24 away from side plate 36. As the motion continues it rides over flat 37 and into notch 18. In the other direction of rotation of lid 14 there is no camming provision and the pin 20 and notch 18 are locked. We have found that pin 20 will shear off if a strenuous attempt is made to reclose lid 14. This is beneficial because it prevents reuse of cassette 10 which might cause dangerous cross contamination.

Now consider the configuration of the gel slab formed in gel cavity 28. Resolution of the DNA patterns produced by the direct blotting method can be enhanced by appropriately shaping the gel. Ideally, the best resolution results when all DNA fragments of a given size are captured at the same location on the membrane. In practice, this does not occur using a gel with a rectangular cross section because similar DNA fragments are distributed across the thickness of the gel, and are spread across a distance equal to the thickness of the gel when captured by the membrane. Furthermore, if the speed of the membrane is slow, fragments of DNA which can normally be identified as different from each other by the traditional Southern blotting procedure may not be resolved as separate because of pattern overlap.

The gel described herein has an internal shape which provides different path lengths for the DNA fragments to allow similar DNA fragments to be captured in close proximity to each other by a membrane positioned perpendicular or nearly so to the major axis of the gel.

Figure 9:
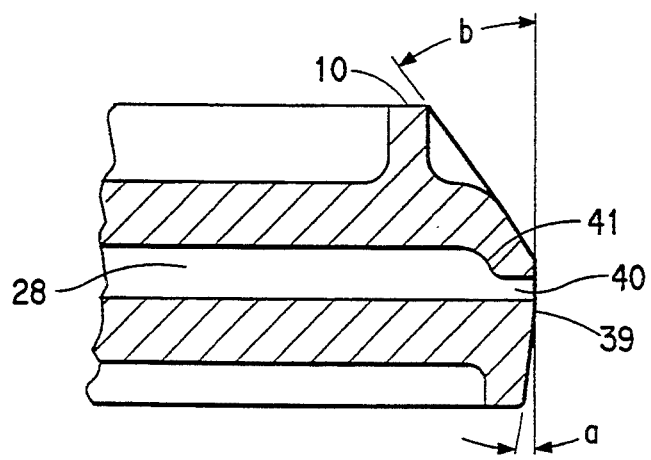
FIG. 9 is an enlarged cross section of the cassette taken on the line 9—9 of FIG. 2 showing details of the gel cavity.

For purposes of this description, the gel is assumed to be oriented horizontally (in the apparatus for which cassette 10 is intended it is held within 2 degrees of horizontal merely to provide drainage), and the membrane vertically, with upward motion. The bottom surface of the gel is a horizontal plane. The upper surface of the gel is parallel to the bottom for most of its expanse, but tapers towards the bottom surface near the end which contacts the membrane. This is best seen in FIG. 9. After the end of the taper, the upper surface parallels the bottom surface for a short distance before reaching the end, the thickness of the gel having been greatly reduced by the taper. DNA fragments positioned near the bottom surface of the gel have a straight path to the gel, whereas fragments near the upper surface have a more convoluted, and thus longer, path. The speed and direction of the membrane can be set such that DNA fragments having a longer path length which exit from the gel at a later time can be captured at the same point on the membrane as the earlier DNA fragments, the membrane having travelled in the interim so that the capture point coincides with the point at which the fragments exit from the gel. It can now be understood that this shape can be used along with an appropriate electric field and membrane speed to achieve improved DNA pattern resolution. Although timing of the arrival of a DNA fragment at the membrane is primarily related to the distance it travels, there are less significant effects that should be considered for a fuller understanding. The speed of travel of a DNA fragment depends upon the strength of the electric field through which it travels, and its mobility which is a function of its size, shape, and the composition of the gel. As the cross section of the gel changes in the region where it tapers, the electric field also changes in intensity.

Figure 3:
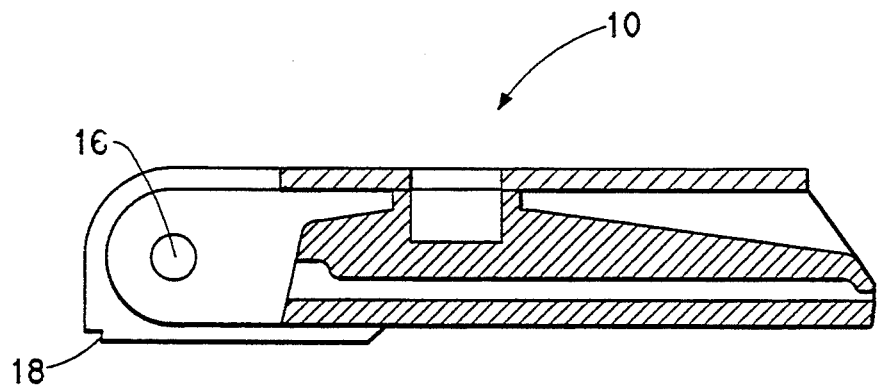
FIG. 3 is a cross-sectional view similar to FIG. 2 but shown with a closed lid.

In use cassette is closed, as shown in FIGS. 3 and 4 and inserted into fixture 100 so that the openings into gel cavity 28 are closed by rubber pads 104. Comb 200 (see FIG. 6), which is fabricated from an elastomeric material, is inserted into cassette 10 so that the inside of slot 26 is contacted by wall 202, the inside of comb well 46 is contacted by wall 204 and each of comb teeth 206 enters a comb guide 48. Teeth 206 are of a length such that they penetrate part way into cavity 28. Thus during the casting process they form a mold insert that will create the wells in the gel slab that are to be charged with innoculant. Each tooth 206 forms a leakproof seal with its corresponding comb guide 48 so that gel does not leak out during casting. Excess gel is not left in the neighborhood of the well so that there are no particles which might fall into the well and thus interfere with the process.

Having reference to FIG. 5, the needle of a syringe (not shown) which is loaded with gel forming liquid (agarose for one) is inserted through a hole 105 in back wall 108 of fixture 100 and passes through a similar hole (not seen) in rubber pad 108 so that gel forming liquid can be discharged into expanded gel entry port 44 and cavity 28 filled. At least one hole 105 is needed, we prefer two as shown. The second hole 105 may be used as a vent. Slot 40 is closed by the other rubber pad 104 which is supported by front wall 106 of fixture 100. Thus a slab of gel is formed completely bounded and having a selected number of wells. Lip 102 acts as a convenient handle for the combined cassette/fixture.

In use, a thin slab of agarose is cast in a four sided slot. A comb penetrates the top side to form the wells. The open end of the cavity holding the gel which is upstream relative to the direction of electrophoretic migration opens into a buffer chamber. The other open end, which contacts the moving membrane, is tapered internally on the side away from the direction of motion of the membrane near the contact end for band concentration. The cassette itself is tapered externally away from the direction of motion of the membrane for clearance. A combination shipping cover/handle/lid is pivoted near the upstream end of the cassette. The entire cassette is held in a clip for shipping which protects the ends and bottom. Elastomeric pads at either internal end of this clip seal both upstream and downstream exposed ends of the gel during shipping and storage.

After casting, the gel is allowed to congeal and the entire assembly is placed in a vapor impervious bag for shipping and storage.

In the closed position the cassette is well protected against physical damage. In use the clip (and a well-forming coma) are removed first. The lid is pivoted to the open position where a permanent (non-releasable) snap lock is provided permitting the lid to serve as a handle for insertion and removal of the cassette into and out of a Separation and Transfer (S/T) module. The non-releasable function of this lock prevents reuse of contaminated gel. Bosses can be provided on the cassette to releasably snap into the S/T structure to secure the cassette in place and bias the cassette toward the fully inserted position. In the instant apparatus this function is provided by contours on the end of the hinge pivots. The lid can be provided with a releasable snap lock in the closed position. Additionally the functions of the clip can easily be incorporated in the lid.

The consumer opens the bag, removes the assembly of cassette 10 with comb 200 in place and fixture 100, removes fixture 100 and comb 200, opens lid 22, and inserts cassette 10 into the automatic separation and transfer apparatus designed for its use.

In such automatic apparatus as disclosed in U.S. Pat. No. 5,234,559 the surface upon which cassette 10 rests by design may be tilted below horizontal in the direction of insertion to provide drainage. We use an angle of 2 degrees. We prefer to remove this same 2 degrees from the front wall 38 of cassette 10. We further prefer to remove an additional 5 degrees from that wall (see angle "a" in FIG. 9) so that the contact between the transfer membrane which moves upwardly and the wall 38 takes place just before the end of the gel in slot 40 on surface 39.

The presence of a taper in cassette 10 shown by angle "b" in FIG. 9 allows the membrane to wrap slightly around the end of the cassette and reduces the vertical distance the cassette is in contact with the membrane in the neighborhood of the gel, thus assuring good contact. The taper also mates with a similar taper in the S/T module and in conjunction with the forward-biasing action of the boss on the end of hinge pivots 16, locates the cassette 10 in the apparatus precisely and securely.

What is claimed is:

1. A gel cassette in which molecular fragments in a solution are separated electrophoretically therein, comprising:
   (a) a gelatinous substrate for containing the molecular fragments for separation at a first end thereof and configured sufficient to concentrate similar separated molecular fragments at a second end thereof; and
   (b) containment means which supports said gelatinous substrate; wherein said gelatinous substrate (a) further comprises a top surface through which the molecular fragments are added and a bottom surface which contacts said containment means, said top and bottom surfaces being essentially parallel to one another in the region of said first end and said top and bottom surfaces being essentially non-parallel to one another in the region of said second end so that said gelatinous substrate is narrower in cross section between said top and bottom surfaces at said second end than at said first end.

2. The gel cassette of claim 1 wherein said top and bottom surfaces form a taper in the region of said second end.

3. The gel cassette of claim 2 wherein said top surface is tapered.

4. The gel cassette of claim 1 wherein said gelatinous substrate (a) further contacts peripheral portions therebetween said top and bottom surfaces, and wherein said containment means (b) further comprises
   (i) a base portion which supports said substrate (a) along said bottom surface thereof;
   (ii) a plurality of walls positioned essentially perpendicularly to said bottom surface to support said substrate (a) along said peripheral portions thereof;
   (iii) a top portion which bears upon said top surface of said substrate; and
   (iv) a well portion positioned relative to said top surface suitable for casting integral wells within said substrate (a) adapted to contain the solution including molecular fragments for electrophoresis.

5. The gel cassette of claim 4 wherein said walls (ii) further include at least one aperture therethrough in the region of the first end of said substrate (a) adapted for introduction of gel and an apeture therethrough in the region of the second end of said substrate (a) adapted for discharge of the electrophoretically separated molecular fragments to a suitable medium.

6. The gel cassette of claim 4 wherein said well portion (iv) comprises a comb having a plurality of teeth which cast said integral wells when contacted by said gelatinous substrate.

7. The gel cassette of claim 4 wherein said containment means (b) further comprises a cover portion in hinged relation to said base portion and moveable from a first position wherein said cover portion extends over said top portion of said gel cassette, to a second position wherein said cover portion exposes said top portion sufficient to install the gel cassette in associated electrophoretic apparatus.

8. The gel cassette of claim 7 wherein said base portion and said cover portion lock into said second position.

* * * * *